United States Patent
Bier et al.

[11] Patent Number: 5,980,839
[45] Date of Patent: Nov. 9, 1999

[54] APPARATUS AND PROCESS FOR CONDUCTING COMBINATIONAL CHEMICAL SYNTHESES

[75] Inventors: Milan Bier; German Eduardo Fuentes; Rodolfo Bacheleir Marquez; Anthony Ralph Ford, all of Tucson, Ariz.

[73] Assignee: Protein Technologies, Inc., Tucson, Ariz.

[21] Appl. No.: 09/022,047

[22] Filed: Feb. 11, 1998

[51] Int. Cl.⁶ .......................................................... B01J 8/08
[52] U.S. Cl. .................. 422/209; 435/286.7; 435/288.4; 436/518
[58] Field of Search .............................. 435/286.7, 288.4; 436/518; 422/209

[56] References Cited

PUBLICATIONS

A. Furka et al., Int'l Abstract No. P–168, Xth Int'l Symp. Med. Chem., Budapest, Hungary, Aug. 1988.
A. Furka et al., *Int'l J. Peptide Protein Res.*, vol. 37, pp. 487–493, 1991.
A. Furka et al., "Proteins and Nucleic Acids in Three Dimensions," 14th Int'l Congress of Biochemistry, Abstracts, vol. 5, FR: 013, Prague, Czechoslovakia, Jul. 15, 1988.
R.N. Zuckermann et al., *Int'l J. Peptide Protein Res.*, vol. 40, pp. 497–506 (1992).
Z. Moukheiber, "A Hail of Silver Bullets," *Forbes*, pp. 76–81, Jan. 26, 1998.
C. Wrotnowski, "Important Trends and Developments in Biotechnology Instrumentation Systems," *Genetic Engineering News*, pp. 6 and 35, Dec. 1997.
S. Danheiser, "Laboratory Automation and Robotics to Play A Major Role in the Drug Discovery Process," *Genetic Engineering News*, pp. 1 & 10, Dec. 1997.

*Primary Examiner*—Keith D. MacMillan
*Attorney, Agent, or Firm*—Kenyon & Kenyon

[57] ABSTRACT

The objective of combinatorial chemical synthesis is the preparation of a very large number of different molecular entities by a randomized process of sequential chemical syntheses. The present invention provides a combinatorial vessel comprising a reaction region and a mixing region, adjacent to each other, which can be used to practice combinatorial chemical synthesis. The reaction region comprises a plurality of reaction cavities, in which a plurality of different chemical reactions may be performed simultaneously on resin beads. The resin beads are then transferred to the mixing region and mixed into a single group. Then, the resin beads are transferred into the reaction cavities. The process of performing reactions, transferring to the mixing region, mixing, and transferring to the reaction region can be repeated multiple times to obtain a large number of resin beads, each of which has been exposed to a series of reactions different from most of the other resin beads.

32 Claims, 7 Drawing Sheets

APPARATUS AND PROCESS FOR CONDUCTING COMBINATIONAL CHEMICAL SYNTHESES

FIELD OF THE INVENTION

The present invention relates to an apparatus and a process for conducting combinatorial chemical syntheses in the apparatus, wherein multiple simultaneous reactions and the mixing of resin beads are carried out in the apparatus.

BACKGROUND OF THE INVENTION

In the search for new drugs, combinatorial chemistry has assumed a major role. Combinatorial chemistry involves synthesizing a large number of different molecular structures, which can then be screened for biological activity. The most promising structure(s) possessing a desired pharmacological activity can be identified and isolated for further experimentation and/or commercial applications. In principle, an astronomically high number of new molecular structures can be synthesized and screened. Combinatorial chemistry therefore requires a way to easily and inexpensively synthesize a large number of different molecular structures. Polypeptide and polypeptoid molecules are among the molecules that may be synthesized using combinatorial chemistry.

One method of synthesizing a large number of different molecular structures simultaneously involves the use of resin beads suspended in solvent. A large number of resin beads are divided into groups, and a different reaction is performed on each group. The resin beads are then combined into a single group and mixed. This process is repeated several times, after which each resin bead has been exposed to a sequence of reactions different from most of the other resin beads, such that each resin bead has bound molecules with a structure different from the molecules bound to most of the other resin beads.

At first, combinatorial chemistry was manually implemented. See A. Furka et al, Abstract No. P-168, Xth Intl. Symp. Med. Chem. in Budapest, Hungary, August 1988 and A. Furka et al, Int. J. Peptide Protein Res., Vol. 37, pp 487–493, 1991. However, manual implementation is slow and labor intensive.

R. N. Zuckermann et al., Int. J. Peptide Protein Res., Vol. 40, pp.497–506 (1992), discloses the use of automated methods of performing combinatorial chemistry based on robotic transfer of fluids. However, single robotic arm servicing a number of individual reaction vessels causes undesirable time delays and precludes simultaneous reactions. Also, repeated handling of resin beads by the robotic arm may damage or break down some of the resin beads. In addition, providing free access for the robotic arm may require exposing the reaction vessels to the surrounding environment, making it difficult to achieve a controlled environment. Without a controlled environment, reagents may be exposed to humidity, oxygen, or other environmental elements to which they may be sensitive. Lack of a controlled environment may also present significant hazards because noxious solvents, such as dimethylsulfoxide or methylene chloride, may be released into the environment.

Sugarman et al. (U.S. Pat. No. 5,503,805) discloses an apparatus wherein resin beads suspended in solvent are transferred between a "parent vessel" and one or more reaction vessel banks by valves, tubing, and argon pressure. While avoiding the need for robotic transfer of fluid, the apparatus is very complex, and requires transfer of resin bead suspensions between distant containers, which may damage the resin beads.

SUMMARY OF THE INVENTION

An object of the present invention is to provide an apparatus and a process for conducting automated combinatorial chemical syntheses in a single, controlled environment, wherein multiple simultaneous reactions and the mixing of resin beads are carried out in the apparatus, and wherein the resin beads are transferred between a reaction region and a mixing region without the use of robotics and without damaging transport through valves and tubing.

In accordance with an embodiment of the present invention, a vessel for combinatorial chemical synthesis is provided that includes a reaction region comprising a plurality of individual reaction cavities, each of the cavities having a port adapted to supply or remove reagents, solvents, gases and/or vacuum suction to the reaction cavity; and a mixing region which is disposed adjacent to the reaction region.

In accordance with an embodiment of the present invention, a process for carrying out combinatorial chemical synthesis in a single vessel is provided that includes the steps of: distributing resin beads into each of a plurality of reaction cavities disposed within the vessel; performing a reaction in each of the reaction cavities on the resin beads; transferring the resin beads from each of the reaction cavities into a mixing region disposed within the vessel; mixing the resin beads in the mixing region; and transferring the resin beads from the mixing region back to the reaction cavities; wherein the steps of transferring are accomplished by gravity or the buoyancy of the resin beads in a liquid; wherein the steps of distributing resin beads into each of the plurality of reaction cavities disposed within the vessel, performing a reaction in each of the reaction cavities, transferring the resin beads from each of the reaction cavities into the mixing region disposed within the vessel, and mixing the resin beads in the mixing region; and transferring the resin beads from the mixing region back to the reaction cavities are conducted at least once.

In accordance with an embodiment of the present invention, a vessel for combinatorial chemical synthesis is provided that includes: a reaction region comprising a plurality of individual reaction cavities; a mixing region which is disposed adjacent to the reaction region; means for performing a reaction on resin beads in each of a plurality of reaction cavities; means for transferring the resin beads from the plurality of reaction cavities into a mixing region adjacent to the reaction cavities; means for mixing the resin beads in the mixing region; and means for transferring the resin beads from the mixing region to the reaction cavities.

DETAILED DESCRIPTION OF THE INVENTION

Figure 1:
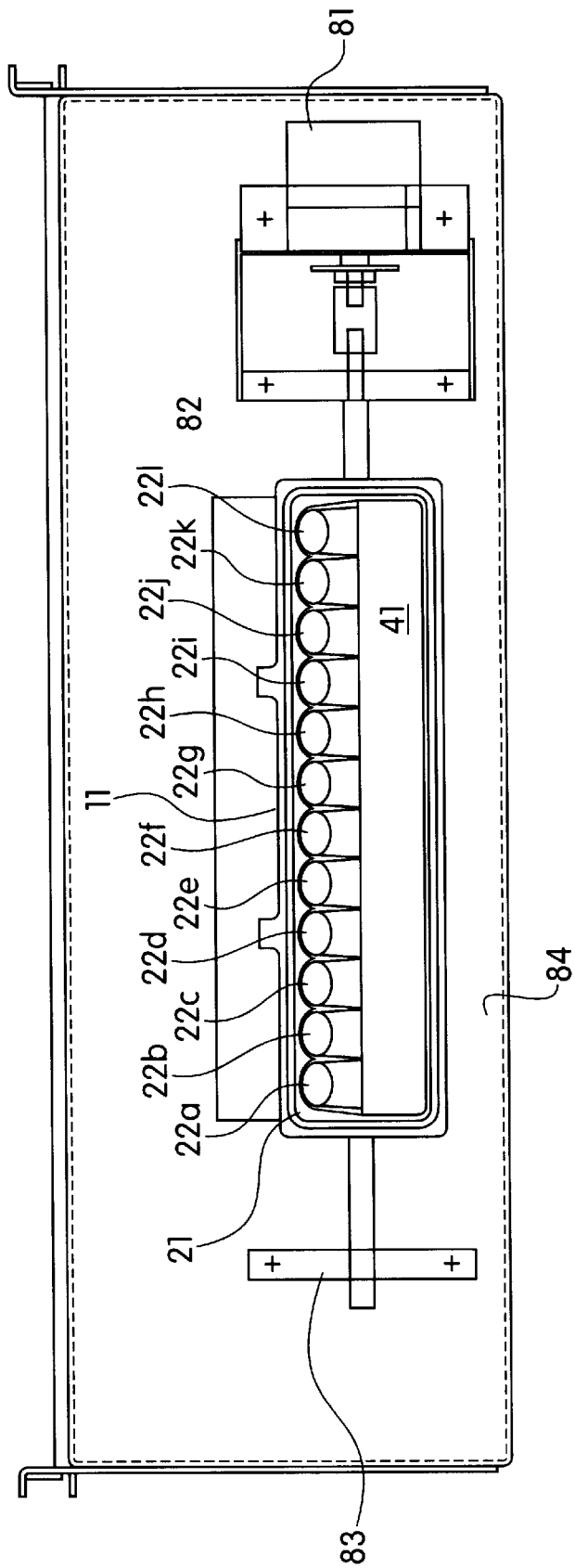
FIG. 1 shows a front view of a linear embodiment of the present invention.

The combinatorial vessel of the present invention is provided with a reaction region comprising an array of individual reaction cavities, each cavity being provided with means for the addition of specified reactants, solvents, pressurized gases, vacuum suction, etc. The pressurized gases can be used not only to control the atmosphere in the vessel but also to stir resin bead suspensions contained in the cavities. Ideally, the vessel would contain as many individual cavities as there are reactants. Above the liquid level reachable in the reaction cavities there may be other openings, such as outlets for the release of pressurized gases. Frits at all inlets and outlets prevent the loss of resin beads from the vessel. The switch from reactants, solvents, or gases can be controlled with valves, external to the combinatorial vessel, and operated by a programmable computer. In addition to the reaction region the vessel contains a mixing region within which the contents of all the reaction cavities can be mixed before being redistributed to the reaction cavities for the next reaction step. The reaction region and the mixing region are adjacent to each other, and are contained within the single combinatorial vessel. This adjacency allows resin beads suspended in solvent to be transferred between the reaction region and the mixing region using gravity or the buoyancy of the resin beads in solvent, which are very simple and gentle methods of transfer that minimize any possible resin bead degradation.

The whole vessel, including the array of reaction cavities and the mixing region, can be sealed by a cover which is preferably a glass plate permitting visual inspection of its contents. At the end of the synthetic steps, the cover can be removed for the collection of all resin beads. Alternatively, the vessel can also be provided with an opening sealed during the reactions, but usable for resin bead addition or collection.

If desired, the contents of individual reaction cavities can be heated in a variety of ways. Small immersion heaters can be imbedded, or external electric heat elements applied. It is also possible to heat the contents of individual cavities by focusing infrared light through the cover.

The present invention comprises a combinatorial vessel having a reaction region, which includes a plurality of reaction cavities, and a mixing region adjacent to each other. Adjacent as used herein generally means that the reaction cavities open into the mixing region such that the contents of the reaction cavities can be transferred to the mixing region, and vice-versa, by methods which do not rely on robotics or transfer through tubing. Such methods include rotating the combinatorial vessel, and adding or removing a liquid in which the contents of the reaction cavities and/or mixing region are buoyant. The present invention includes any number of physical geometries, of which a few are illustrated with reference to the following embodiments, which are not intended to limit the scope of the invention.

FIG. 1 shows a front view of an example of a linear embodiment of the present invention. A linear combinatorial vessel 11 is coupled to a horizontal axle 82. Linear combinatorial vessel 11 comprises a linear mixing region 41, adjacent to a linear reaction region 21, which further comprises 12 reaction cavities 22, including reaction cavities 22a, 22b, 22c, 22d, 22e, 22f, 22g, 22h, 22i, 22j, 22k and 22l. Horizontal axle 82 is rotatably mounted between a stepping motor 81 and a pivot 83. Stepping motor 81 and pivot 83 are mounted on a supporting platform 84. Linear combinatorial vessel 11 and horizontal axle 82 may also be mounted such that linear combinatorial vessel 11 can be tilted, i.e., rotated about an axis other than the axis of axle 82, preferably about a horizontal axis normal to the axis of axle 82. Alternatively, platform 84 may be movably mounted such that linear combinatorial vessel 11 may be moved by moving platform 84. Preferably, the movement of combinatorial vessel 11 may be controlled by a computer.

Figure 2:
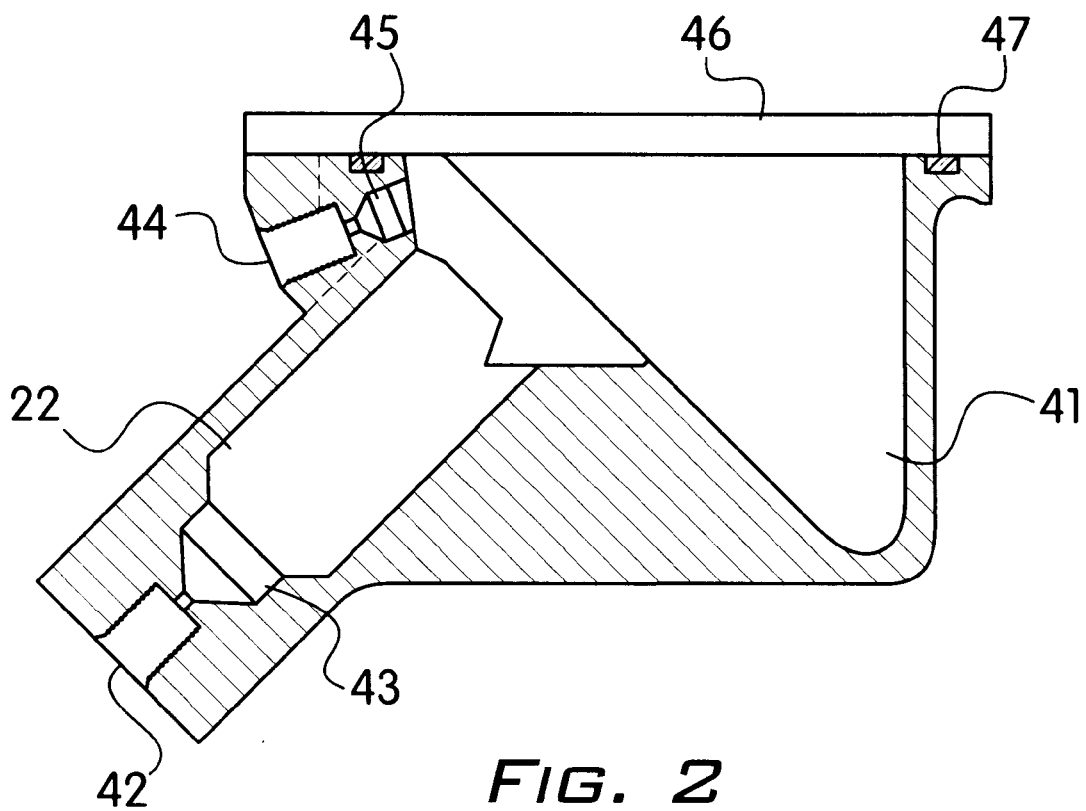
FIG. 2 shows a side view of a cross-section of the embodiment of FIG. 1.

FIG. 2 shows a side view of the linear embodiment of FIG. 1. Reaction cavity 22 opens into linear mixing region 41. Each reaction cavity 22 has a port 42 adapted to supply reagents, solvents, gases, and/or vacuum suction from flexible tubing (not shown) into reaction cavity 22, and to drain reaction cavity 22. A frit 43 disposed between port 42 and reaction cavity 22, preferably made of glass or plastic, prevents resin beads in reaction cavity 22 from passing through port 42. One or more ports 44 may be adapted to vent gas from or supply solvents to reaction cavity 22 and/or linear mixing region 41. A frit 45 prevents resin beads from passing through port 44. The supply of reagents, solvents, gases, or vacuum suction, and the draining thereof, through ports 42 and 44 is preferably controlled automatically, for example by a computer. A plate 46 covers linear combinatorial vessel 11, and an o-ring 47 provides an air-tight seal between plate 46 and linear combinatorial vessel 11. An air tight seal allows a controlled environment to be achieved within combinatorial vessel 11. Plate 46 may be attached to linear combinatorial vessel 11 by any conventional method.

Linear combinatorial vessel 11, as well as any vessel of the present invention, can be made, for example, from any material resistant to the chemical reagents and solvents used in peptide chemistry, by any suitable method, such as machining or molding. For example, linear combinatorial vessel 11 may be made of glass, stainless steel, teflon or teflon composites, or a suitable plastic such as polypropylene or polyphenylene sulfide (PPS). Plate 46 can be made of materials suitable for linear combinatorial vessel 11, and is preferably made of a transparent material such as glass, which allows visual inspection of the contents of linear combinatorial vessel 11.

FIGS. 3A–3C show the rotation of linear combinatorial vessel 11 of the linear embodiment of FIG. 1 around axle 82. FIG. 3A illustrates the orientation of linear combinatorial vessel 11 when the bulk of the contents are in reaction cavities 22, wherein chemical reactions, different for each reaction cavity 22, may be performed. FIG. 3B illustrates a 'neutral' orientation, suitable for inspection of the contents of linear combinatorial vessel 11. FIG. 3C illustrates the orientation of combinatorial vessel 11 when the bulk of the contents are in linear mixing region 41, wherein resin beads and the solvent in which they are suspended may be mixed. Ports 42 and 44 are adapted to be attached to flexible tubes such that combinatorial vessel 11 may be rotated about axle 82 without interference from the tubes. A tube connector 48 attached to ports 42 and 44 may be used to attach tubes to ports 42 and 44. The range through which linear combinatorial vessel 11 can be rotated may be limited to prevent the detachment of tubes.

Figure 3:
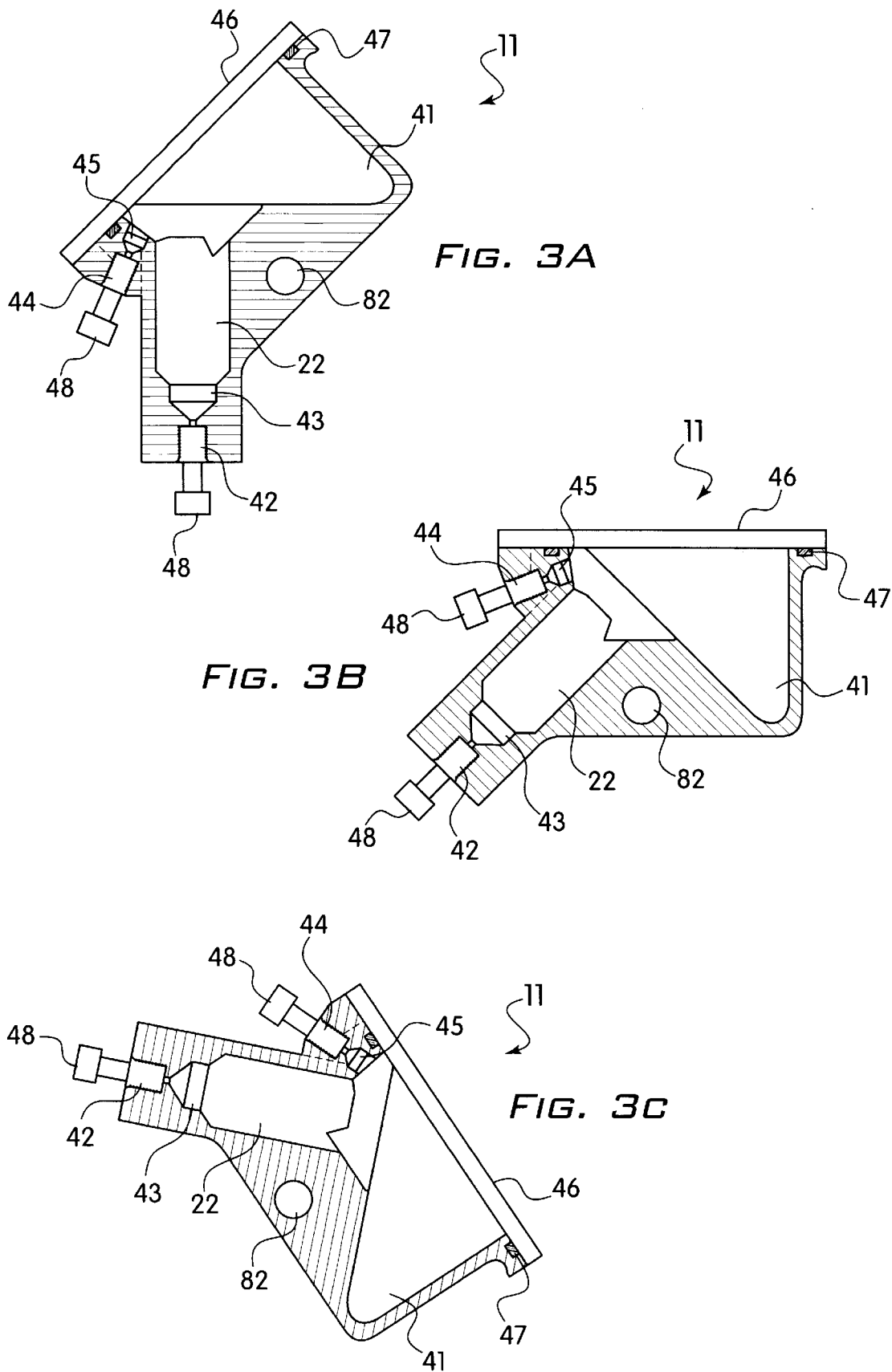
FIGS. 3A–3C show a side view of a cross-section of the embodiment of FIG. 1 in various orientations.

The operation of the linear embodiment of FIGS. 1–3 will now be described with reference to FIGS. 1–3. Suitable resin beads are loaded into linear combinatorial vessel 11. Any resin beads known to the art may be used, such as Fmoc Amino Acid Wang resin beads, available from Novabiochem Corp. of San Diego, Calif. The resin beads are distributed approximately uniformly into reaction cavities 22, either manually or by suspension in solvent and mixing in linear mixing region 41, followed by the transfer of the resin beads and the solvent in which they are suspended into reaction cavities 22 prior to performing any reactions. Linear combinatorial vessel 11 is then covered with plate 46.

Reagents for the desired chemical reaction are added to the individual reaction cavities 22 through ports 42, and allowed to react on the resin beads in the reaction cavity 22. Preferably, a different reagent is added to each reaction cavity 22. The contents of individual reaction cavities 22 may be stirred by the addition of gases through ports 42. The gas may be vented through port(s) 44, which is preferably disposed such that it remains above the level reached by the reagents. After a period of time suitable for completion of the reactions has passed, the reagents are drained through ports 42, and the contents of all reaction cavities 22 are rinsed with solvents.

Linear combinatorial vessel 11 is then rotated about axle 82 to the position shown in FIG. 3C. Gravity then acts to transfer the resin beads in reaction cavities 22, and the solvent in which they are suspended, to linear mixing region 41. Solvents may be added through ports 42 before, during, and after this rotation to ensure that the bulk of the resin beads in reaction cavities 22 are transferred to linear mixing region 41.

Linear mixing region 41 is then rocked and/or tilted back and forth several times to mix the resin beads, and the solvent in which they are suspended, uniformly throughout linear mixing region 41. Rocking is a back and forth rotation of linear combinatorial vessel 11 about axle 82 such that the contents of linear mixing region 41 remain in linear mixing region 41. For example, rocking includes, but is not limited to, the rotation of linear combinatorial vessel 11 back and forth between the positions shown in FIGS. 3B and 3C. The rocking and/or tilting may also result in an approximately uniform distribution of resin beads in linear mixing region 41. A solvent, including a solvent mixture, may be introduced into linear mixing region 41 through port 44 to facilitate mixing. The solvent may be such that the resin beads float in the solvent, isopicnic with the resin beads such that the resin beads neither float nor sink, or such that the resin beads sink in the solvent. Linear combinatorial vessel 11 may then be tilted and/or rocked back and forth several times such that the resin bead suspension is distributed approximately linearly along linear mixing region 41.

Linear combinatorial vessel 11 is then rotated about axle 82 to the position shown in FIG. 3A. Gravity then acts to transfer the resin beads, and the solvent in which they are suspended, into reaction cavities 22. Solvent may be added through ports 44 before, during, and after this rotation to ensure that the bulk of the resin beads are transferred into reaction cavities 22.

The use of gravity to transfer resin beads and the solvent in which they are suspended from reaction cavities 22 to linear mixing region 41, and from linear mixing region 41 into reaction cavities 22, where reaction cavities 22 are adjacent to linear mixing region 41, is a very quick and convenient method of transfer that minimizes damage to the resin beads.

The sequence of performing reaction on resin beads in reaction cavities 22, transferring the resin beads to linear mixing region 41, mixing the resin beads in linear mixing region 41, and transferring the resin beads to reaction cavities 22 can then be repeated as desired. During each iteration, each reaction cavity 22 should contain a mixture of resin beads from each reaction cavity 22 during the previous iteration. After several iterations, each resin bead should therefore be exposed to a sequence of reactions that is different from that to which most of the other resin beads are exposed. After the desired number of reactions has been performed, plate 46 may be removed and the resin beads extracted from linear combinatorial vessel 11.

Figure 4:
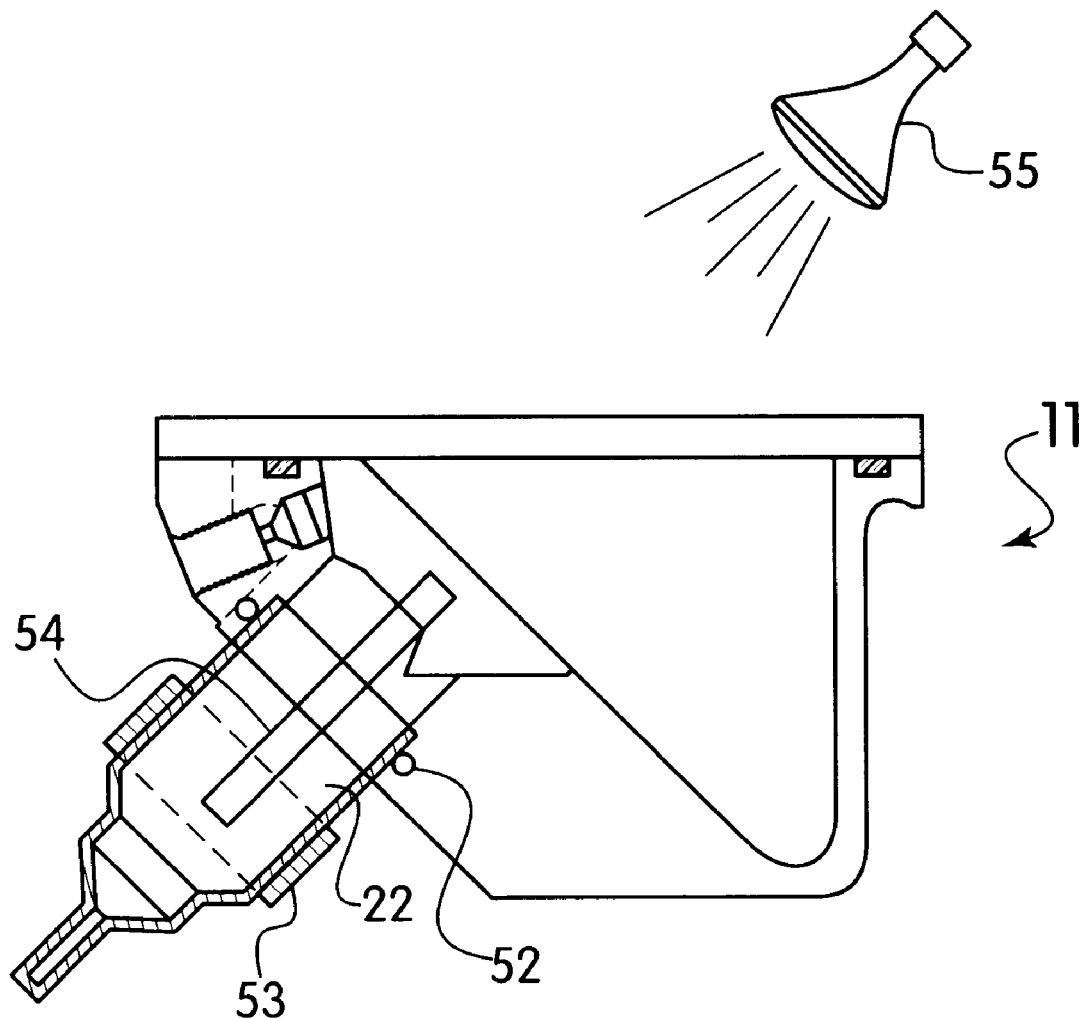
FIG. 4 shows a side view of a cross-section of the embodiment of FIG. 1, including temperature control devices.

FIG. 4 shows a side view of the linear embodiment of FIG. 1, showing several embodiments of temperature control devices adapted to heat and/or cool the contents of reaction cavity 22.

For example, temperature control wrap 53 may be wrapped around reaction cavity 22. Temperature control device 53 may be any suitable heating and/or cooling device known to the art, such as an electric heater or a heat exchanger.

Temperature control may also be provided by an immersion device 54. Immersion device 54 may be embedded in the wall of reaction cavity 22. Alternatively, immersion device 54 may protrude into reaction cavity 22 without being embedded in the wall of reaction cavity 22. Immersion device 54 may be any heating and/or cooling element known to the art, such as an electric heater or a heat exchanger.

Temperature control may also be provided by an infrared radiating element 55 disposed near linear combinatorial vessel 11 such that the contents of reaction cavity 22 may be heated by exposure to infrared radiation. Preferably, the part of linear combinatorial vessel 11 through which the infrared radiation is transmitted to the contents of reaction cavity 22 is adapted to transmit infrared radiation. For example, plate 46 or reaction cavity 22 may be made of a material that readily transmits infrared radiation.

Thermal properties may be taken into account when choosing the material of which reaction cavity 22 is made. For example, reaction cavities 22 may be made of glass to minimize the transfer of heat from reaction cavities 22 to other part of combinatorial vessel 11. If reaction cavities 22 are made of a material different from the rest of combinatorial vessel 11, reaction cavities 22 may be secured to the rest of combinatorial vessel 11 in an air-tight manner, for example with o-rings 52.

Various embodiments of the present invention may be adapted to interface with an automated peptide synthesizer, such as the Symphony peptide synthesizer, available from Protein Technologies, Inc, located in Tucson, Ariz. Peptide synthesizers are designed to facilitate controlled reactions in an array of reaction vessels. The Symphony, for example, has twelve output ports to which it can individually and simultaneously deliver reagents, including reagents, solvents and pressurized gases, by using a patented matrix of valves (Barstow et al., U.S. Pat. No. 5,203,368). While the present invention may be adapted to interface with an automated peptide synthesizer, it can also be adapted for use with any other instrument(s) capable of parallel delivery of reagents.

Figure 5:
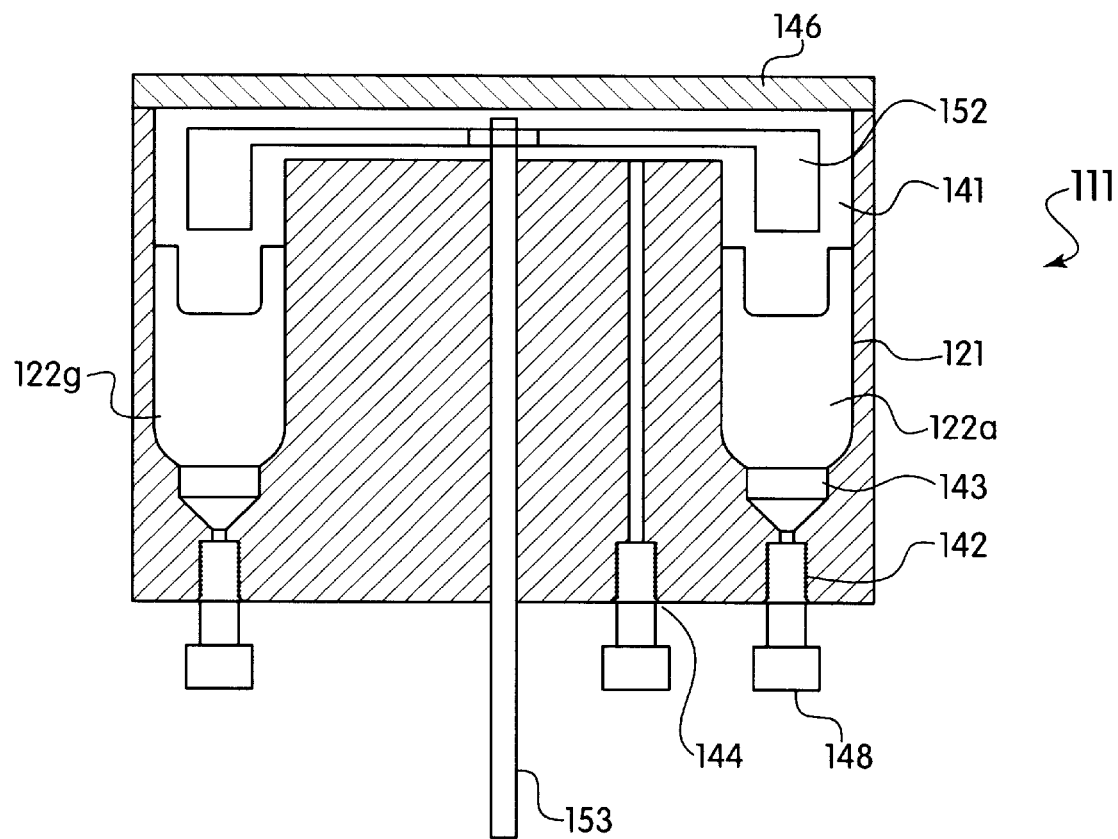
FIG. 5 shows a side view of a cross-section of an annular embodiment of the present invention.

FIG. 5 shows a cross-section of an annular embodiment of the present invention. An annular combinatorial vessel 111 comprises an annular mixing region 141 adjacent to and on top of an annular reaction region 121, which further comprises 12 reaction cavities 122, including reaction cavities 122a, 122b, 122c, 122d, 122e, 122f, 122g, 122h, 122i, 122j, 122k and 122l (only reaction cavities 122a and 122g are shown in FIG. 5). Each reaction cavity 122 has a port 142 adapted to supply reagents, solvents, gases, and/or vacuum suction from flexible tubing (not shown) into reaction cavity 122. A frit 143 disposed between port 142 and reaction cavity 122, preferably made of glass or plastic, prevents resin beads in reaction cavity 122 from passing through port 142. One or more ports 144 may be adapted to vent gas from or supply solvents to annular reaction region 121 and/or annular mixing region 141. The supply of reagents, solvents, gases, or vacuum suction, and the draining thereof, through ports 142 and 144 is preferably controlled automatically, for example by a computer. A tube connector 148 may be used to connect ports 142 and 144 to flexible tubes. A plate 146 covers annular combinatorial vessel 111, and may be attached to annular combinatorial vessel 111 by any conventional method. Covering annular combinatorial vessel 11 with plate 146 such that an air-tight seal is formed allows the atmosphere within linear combinatorial vessel 111 to be controlled as desired. An air tight seal may be formed by any means known to the art. A mixer 152 disposed within annular mixing region 141 is fixed to a mixer shaft 153, which is rotatably mounted in annular combinatorial vessel 111.

Figure 6:
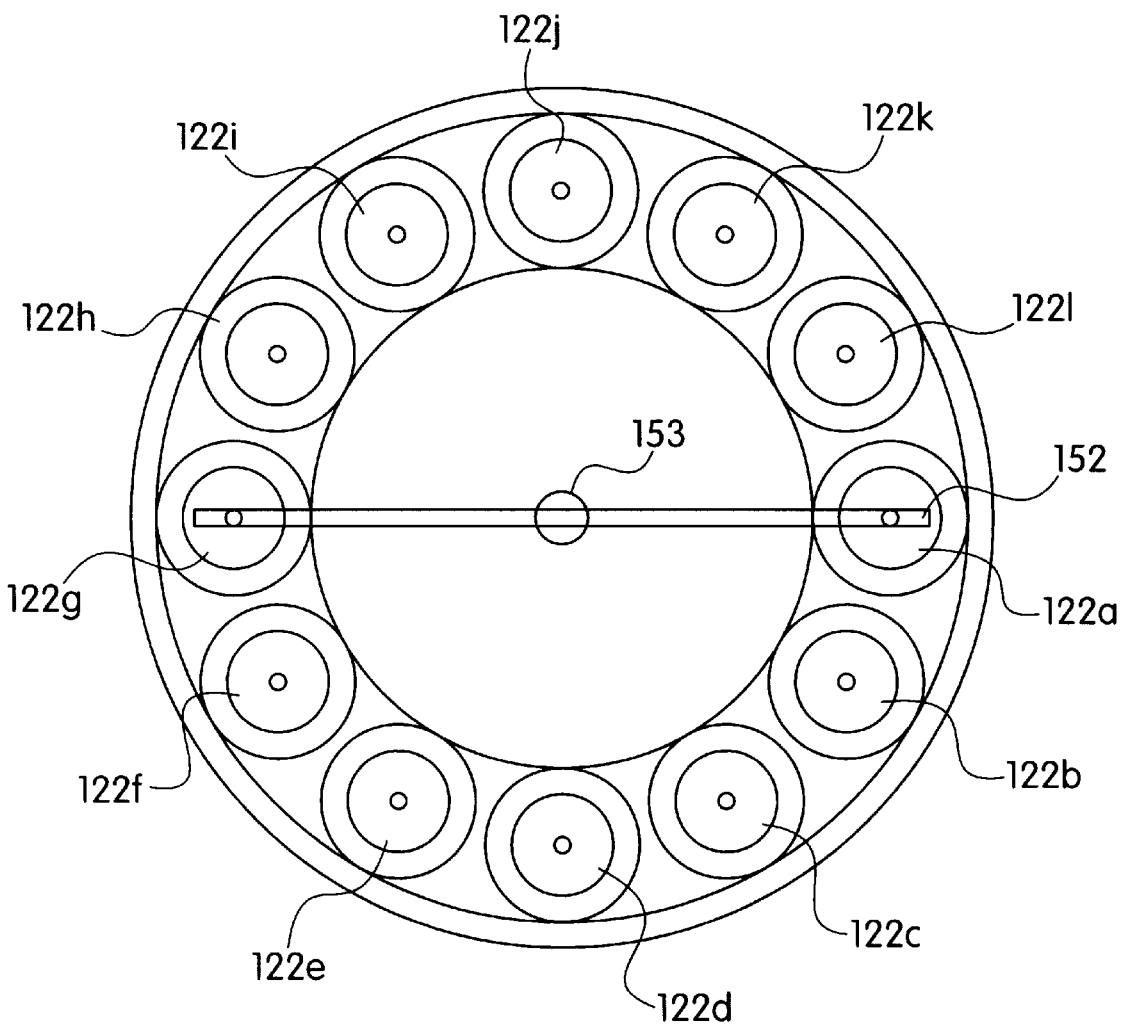
FIG. 6 shows a top view of the embodiment of FIG. 5.

FIG. 6 shows a top view of the annular embodiment of FIG. 5. Reaction cavities 122 are arranged in an annular fashion around mixer shaft 153.

The operation of the annular embodiment of FIGS. 5 and 6 will now be described with reference to FIGS. 5 and 6. Suitable resin beads are loaded into annular combinatorial vessel 111. The resin beads should be distributed approximately uniformly into reaction cavities 122, although an approximately uniform distribution may be achieved by suspending the resin beads in solvent and mixing them in annular mixing region 141, followed by transfer to reaction cavities 122, prior to performing any reactions. Annular combinatorial vessel 111 is then covered with plate 146.

Reagents for the desired chemical reaction are added to the individual reaction cavities 122 through ports 142, and allowed to react on the resin beads in the reaction cavity 122. Preferably, a different reagent is added to each reaction cavity 122. The contents of individual reaction cavities may be stirred by the addition of gases through ports 142. The gas may be vented through port(s) 144, which is preferably disposed such that it remains above the level reached by the reagents. After a period of time suitable for completion of the reactions has passed, the reagents are drained through ports 142, and the contents of all reaction cavities 122 are rinsed with solvents.

A fluid in which the resin beads float is then added to reaction cavities 122 through ports 142 until the fluid level has risen into annular mixing region 141. The buoyancy of the resin beads in the fluid then acts to transfer the resin beads from reaction cavities 122 to annular mixing region 141. A gas may also be added through ports 142 to provide gas agitation to further ensure that the bulk of the resin beads are transferred to annular mixing region 141.

Mixer 152 and mixer shaft 153 are then rotated several times to mix and uniformly distribute the resin beads throughout annular mixing region 141.

The fluid is then drained through ports 142, such that the resin beads are transferred from annular mixing region 141 into reaction cavities 122, distributed about uniformly between the reaction cavities 122. Solvent may be added through port 144 to ensure that the bulk of the resin beads are transferred into reaction cavities 122.

Using the buoyancy of resin beads in selected fluids to transfer resin beads from reaction cavities 122 to annular mixing region 141, and from annular mixing region 141 into reaction cavities 122, where reaction cavities 122 are adjacent to annular mixing region 141, is a very quick and convenient method of transfer that minimizes damage to the resin beads.

The sequence of transferring the resin beads to reaction cavities 122, adding reagents and solvents, transferring to annular mixing region 141 and mixing can then be repeated as desired. After the desired number of reactions has been performed, plate 146 may be removed and the resin beads extracted from annular combinatorial vessel 111. As with the linear embodiment, the result is a large number of resin beads, each of which has been exposed to a series of reactions different from most of the other resin beads.

Mixing the resin beads in suspension by floating and/or gas agitation does not necessarily require an annular combinatorial vessel 111. For example, linear combinatorial vessel 11 of the embodiment of FIG. 1, as well as other embodiments of the present invention, may also be adapted for floating and/or gas agitation.

The present invention is now described with respect to the following examples. However, the scope of the present invention is not intended to be limited thereby.

EXAMPLE 1

An experiment was carried out to prove the effectiveness of the present invention in mixing resin beads and transferring to reaction cavities 22, using combinatorial vessel 11 of the embodiment of FIG. 1. Two batches of derivatized resin beads were first synthesized by conventional techniques, using the Symphony apparatus: 16-AA, a 16 amino acid residue attached to the Fmoc-Ala-Wang resin beads and G-LHRH, a decapeptide, attached to the Rink Amide MBHA resin beads. With linear combinatorial vessel 11 positioned as shown in FIG. 3A, a 300 mg sample of the 16-AA resin beads was deposited in reaction cavity 22a, and a 300 mg sample of the G-LHRH resin beads was deposited in reaction cavity 22l. Linear combinatorial vessel 11 was then covered with plate 46, and 3 ml of a 50/50 mixture of DMF/Methylene Chloride solvent was added to each reaction cavity 22, including reaction cavities 22 containing resin beads. The resin beads, and the solvent in which they were suspended, were then transferred from reaction cavities 22 to linear mixing region 41 by rotating combinatorial vessel 11 to the position shown in FIG. 3C. Linear combinatorial vessel 11 was then rocked around axle 82 five hundred times to mix the resin bead suspension. The resin beads, and the solvent in which they were suspended, were then transferred from linear mixing region 41 to reaction cavities 22 by rotating combinatorial vessel 11 to the position shown in FIG. 3A. The resin beads in each reaction cavity 22 were collected, and cleaved automatically using the Symphony apparatus. The percentage of 16-AA and G-LHRH peptides from each reaction cavity 22 were then measured using a Rainin HPLC system having a Dynamax absorbence detector model UV-1, based on the area under the HPLC peaks. The total of the measured percentage of G-LHRH and the measured percentage of 16AA in a given reaction cavity 22 may be less than 100% due to the presence of impurities that generate small HPLC peaks unrelated to G-LHRH or 16AA. Relative percentage is the measured percentage normalized such that the relative percentages of G-LHRH and 16AA in a given reaction cavity 22 add to 100%. Table 1 shows the measured and relative percentages for each reaction cavity 22.

TABLE 1

| Reaction cavity | measured percentage | | relative percentage | |
| --- | --- | --- | --- | --- |
| | G-LHRH | 16 AA | G-LHRH | 16AA |
| 22a | 55.77 | 38.48 | 59.17 | 40.83 |
| 22b | 44.77 | 37.16 | 54.64 | 45.36 |
| 22c | 57.49 | 35.63 | 61.74 | 38.26 |
| 22d | 55.32 | 36.43 | 60.29 | 39.71 |
| 22e | 54.23 | 38.66 | 58.38 | 41.62 |
| 22f | 58.01 | 36.83 | 61.17 | 38.83 |
| 22g | 58.48 | 39.27 | 59.83 | 40.17 |
| 22h | 60.11 | 35.63 | 62.78 | 37.22 |
| 22i | 56.24 | 34.82 | 61.76 | 38.24 |
| 22j | 58.78 | 34.34 | 63.12 | 36.88 |
| 22k | 60.60 | 33.42 | 64.45 | 35.55 |
| 22l | 61.89 | 35.44 | 63.59 | 36.41 |

Figure 7A:
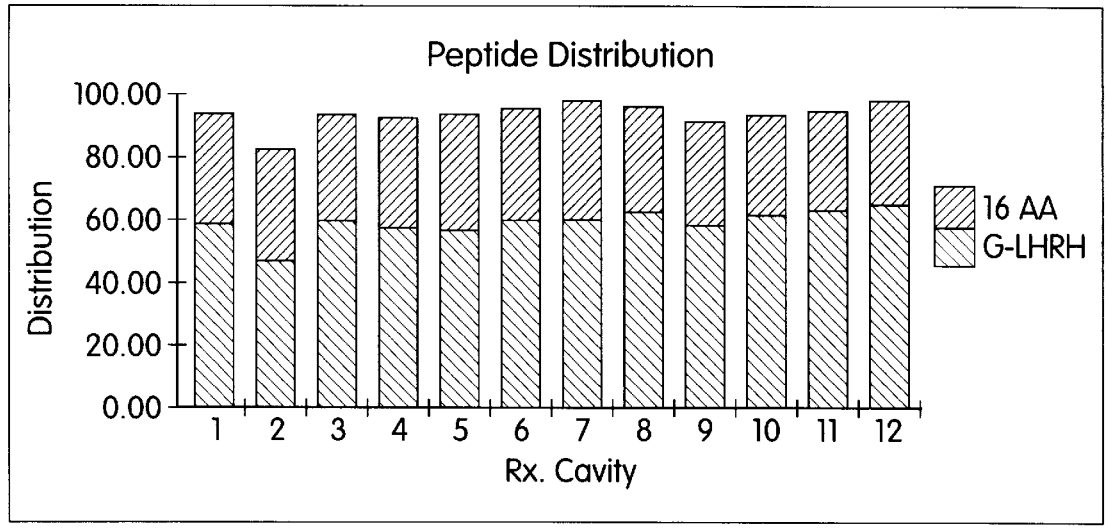
FIGS. 7A and 7B show graphical representations of peptide distributions obtained using the embodiment of FIG. 1.
Figure 7B:
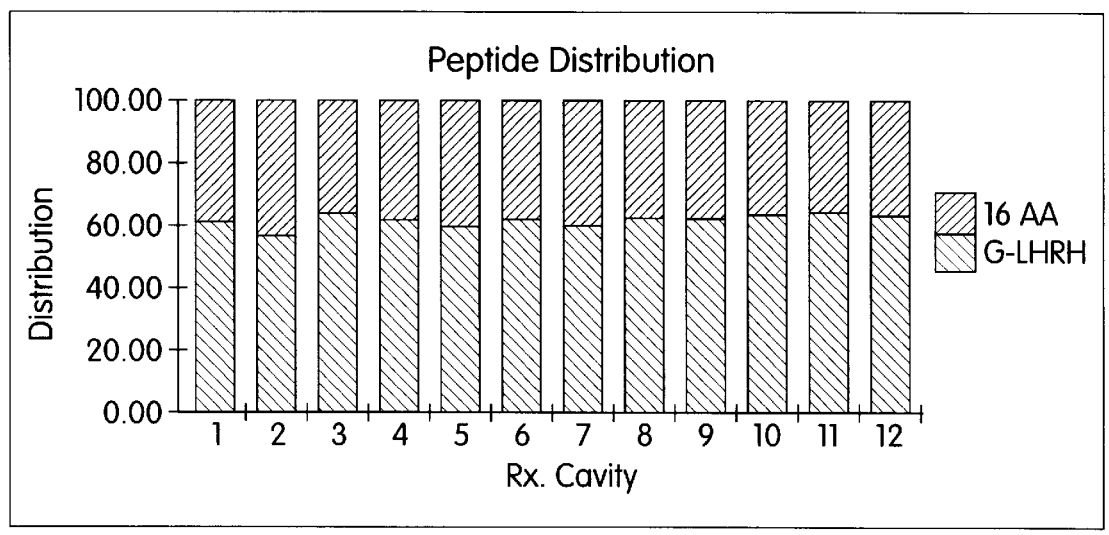

FIG. 7 shows graphs of the data of Table 1. FIG. 7A shows a graph of the measured percentage, and FIG. 7B shows a graph of the relative percentage. Table 1 and FIG. 7 show that G-LHRH and 16AA were distributed approximately uniformly into reaction cavities 22a–22l.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. A vessel for combinatorial chemical synthesis, comprising:
   a reaction region comprising a plurality of individual reaction cavities, each of said reaction cavities having a port adapted to supply or remove reagents, solvents, gases and/or vacuum suction to said reaction cavity; and
   a mixing region disposed adjacent to said reaction region, such that said reaction cavities open into said mixing region.

2. The vessel of claim 1, wherein said vessel is adapted such that resin beads suspended in a solvent may be transferred between said reaction region and said mixing region by changing the relative positions of said reaction region and said mixing region, such that gravity acts on said resin beads suspended in a solvent to cause the transfer.

3. The vessel of claim 2, wherein said reaction cavities form a linear array, and said mixing region comprises a linear trough and forms a linear mixing region extending the full length of said linear array.

4. The vessel of claim 2, wherein said vessel is adapted to rotate.

5. The vessel of claim 2, wherein said vessel is adapted to tilt.

6. The vessel of claim 1, wherein said vessel is adapted such that resin beads suspended in a solvent may be transferred between said reaction region and said mixing region using the buoyancy of the resin beads in the solvent.

7. The vessel of claim 6, wherein said reaction region comprises an annular array of reaction cavities, and said mixing region is disposed on top of said reaction region.

8. The vessel of claim 6, wherein said vessel is adapted to flood with a liquid.

9. The vessel of claim 6, further comprising a mixer mounted on said vessel.

10. The vessel of claim 1, wherein said mixing region has a port adapted to supply or remove solvents, gases and/or vacuum suction to said mixing region.

11. The vessel of claim 10, wherein said ports in said reaction region and said port in said mixing region are adapted to be connected by tubing to an apparatus supplying reagents, solvents and gases through said tubing.

12. The vessel of claim 1, further comprising a temperature control device adapted to heat and/or cool the contents of one or more of said reaction cavities.

13. The vessel of claim 12, wherein said temperature control device is an electric heater.

14. The vessel of claim 12, wherein said temperature control device is a heat exchanger.

15. The vessel of claim 12, wherein said temperature control device is an infrared radiating element.

16. The vessel of claim 12, wherein said temperature control device is an immersion device.

17. The vessel of claim 1, wherein said vessel is made of a material resistant to chemical reagents and solvents customarily used in peptide chemistry.

18. The vessel of claim 17, wherein said vessel is constructed from a material selected from the group consisting of: plastic, glass and stainless steel.

19. The vessel of claim 1, wherein said vessel is used for the combinatorial syntheses of polypeptide and polypeptoid molecules.

20. The vessel of claim 1, wherein said vessel is adapted to be controlled by a computer.

21. The vessel of claim 1, further comprising a plate adapted to cover said vessel and form an airtight seal such that the atmosphere within said vessel may be controlled.

22. A process for carrying out combinatorial chemical synthesis in a single vessel, comprising the steps of:
   distributing resin beads into each of a plurality of reaction cavities disposed within said vessel;
   performing a re action in each of said reaction cavities on said resin beads;
   transferring said resin beads from each of said reaction cavities into a mixing region disposed within said vessel;
   mixing said resin beads in said mixing region; and
   transferring said resin beads from said mixing region back to said reaction cavities;
   wherein said steps of transferring are accomplished by a method selected from the group consisting of (1) changing the relative positions of said reaction region and said mixing region, such that gravity acts on said resin beads to cause the transfer, and (2) using the buoyancy of the resin beads in a liquid;
   wherein said steps of distributing resin beads into each of said plurality of reaction cavities disposed within said vessel, performing a reaction in each of said reaction cavities, transferring said resin beads from each of said reaction cavities into said mixing region disposed within said vessel, and mixing said resin beads in said mixing region; and transferring said resin beads from said mixing region back to said reaction cavities are conducted at least once.

23. The process of claim 22, wherein said steps of transferring the resin beads are accomplished by changing the relative positions of said reaction region and said mixing region, such that gravity acts on said resin beads to cause the transfer.

24. The process of claim 23, wherein said steps of transferring the resin beads are accomplished by rotating the vessel around its horizontal axis.

25. The process of claim 22, wherein:
   said resin beads are buoyant in a liquid;

said step of transferring said resin beads from each of said reaction cavities into said mixing region is accomplished by adding said liquid to said reaction cavities and said mixing region; and said step of transferring said resin beads from said mixing region back to said reaction cavities is accomplished by removing said liquid from said reaction cavities and said mixing region.

26. The process of claim 22, wherein a further reaction is conducted on the resin beads after said step of transferring the resin beads from the mixing region to the reaction cavities.

27. A vessel for combinatorial chemical synthesis, comprising:

a reaction region comprising a plurality of individual reaction cavities;

a mixing region which is disposed adjacent to said reaction region;

means for performing a reaction on resin beads in each of a plurality of reaction cavities;

means for transferring the resin beads from the plurality of reaction cavities into a mixing region adjacent to the reaction cavities;

means for mixing the resin beads in the mixing region; and means for transferring the resin beads from the mixing region to the reaction cavities.

28. The vessel of claim 27, further comprising means for supplying or removing solvents, gases and/or vacuum suction to said reaction cavities.

29. The vessel of claim 27, further comprising means for supplying or removing solvents, gases and/or vacuum suction to said mixing region.

30. The vessel of claim 27, further comprising means for controlling the temperature of said reaction cavities.

31. The vessel of claim 27, further comprising means for automatically controlling said vessel.

32. The vessel of claim 27, further comprising means for controlling the atmosphere within said vessel.

* * * * *